(12) United States Patent
Lee et al.

(10) Patent No.: US 10,200,089 B2
(45) Date of Patent: Feb. 5, 2019

(54) SENSOR SYSTEM AND METHOD

(71) Applicant: General Electric Company, Schenectady, NY (US)

(72) Inventors: Yongjae Lee, Niskayuna, NY (US); Joseph Iannotti, Glenville, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/616,051

(22) Filed: Jun. 7, 2017

(65) Prior Publication Data
US 2018/0359004 A1 Dec. 13, 2018

(51) Int. Cl.
*H04B 5/00* (2006.01)
*G01K 11/22* (2006.01)
*G01L 1/10* (2006.01)
*H04B 15/00* (2006.01)

(52) U.S. Cl.
CPC ............ *H04B 5/0056* (2013.01); *G01K 11/22* (2013.01); *G01L 1/10* (2013.01); *H04B 15/00* (2013.01)

(58) Field of Classification Search
CPC .............................. H04B 5/0056; H04B 15/00
See application file for complete search history.

(56) References Cited

U.S. PATENT DOCUMENTS

| | | | |
|---|---|---|---|
| 4,535,632 | A | 8/1985 | Sinha et al. |
| 5,710,375 | A | 1/1998 | Roger |
| 6,318,147 | B1 | 11/2001 | Steinrueck et al. |
| 6,848,295 | B2 | 2/2005 | Auner et al. |
| 6,999,000 | B2 | 2/2006 | Campbell et al. |
| 7,186,094 | B2 | 3/2007 | Edlund et al. |
| 7,555,370 | B2 | 6/2009 | Breed et al. |

(Continued)

FOREIGN PATENT DOCUMENTS

| | | |
|---|---|---|
| CN | 102252790 | 11/2012 |
| CN | 104483219 | 4/2015 |

(Continued)

OTHER PUBLICATIONS

Hamid et al., "Characteristics and crosstalk of optical waveguides fabricated in polymethyl methacrylate polymer circuit board", OSA Publishing, vol. 55, Issue: 32, pp. 9017-9021, 2016.

(Continued)

*Primary Examiner* — Tuan H Nguyen
(74) *Attorney, Agent, or Firm* — GE Global Patent Operation; Nitin N. Joshi

(57) ABSTRACT

A sensor system includes one or more rotor antennas on a shaft that moves within a stator bracket one or more of around an axis of the sensor system or along the axis of the sensor system, the one or more rotor antennas configured to communicate sensed data with one or more stator antennas on the stator bracket. Each rotor antenna has a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other. The one or more rotor antennas are configured to extend one or more of radially around an outer surface of the shaft of a sensor or along the outer surface of the shaft of the sensor.

17 Claims, 7 Drawing Sheets

(56) References Cited

U.S. PATENT DOCUMENTS

| | | | |
|---|---|---|---|
| 7,732,952 B1* | 6/2010 | Taylor | A61C 17/20 |
| | | | 15/22.1 |
| 7,782,159 B2* | 8/2010 | Beckley | H01P 1/068 |
| | | | 333/24 R |
| 7,936,106 B2 | 5/2011 | Lee et al. | |
| 9,526,163 B2 | 12/2016 | Issakov et al. | |
| 9,537,677 B2 | 1/2017 | Hines et al. | |
| 9,817,014 B2* | 11/2017 | Kozlovski | G01P 3/481 |
| 2002/0011099 A1 | 10/2002 | Domens et al. | |
| 2009/0185658 A1 | 7/2009 | Katcha et al. | |
| 2013/0130362 A1 | 5/2013 | Hines et al. | |
| 2017/0008623 A1 | 1/2017 | Lee et al. | |

FOREIGN PATENT DOCUMENTS

| | | |
|---|---|---|
| CN | 105890661 A | 8/2016 |
| EP | 2688078 A1 | 1/2014 |
| WO | 2005108744 | 11/2005 |
| WO | 2012100579 A1 | 8/2012 |

OTHER PUBLICATIONS

J.-M. Boccard, et al, "Near-field interrogation of SAW resonators on rotating machinery", J. Sens. Sens. Syst., 2, 147-156, 2013.
"Connecting Rod Wireless Strain Measurement", IR Telemetrics, http://www.irtelemetrics.com.connecting_rod_strain_wireless_measurement/connecting_rod_strain_wireless_measurement.html, 2016.
European Search Report and Opinion issued in connection with corresponding EP Application No. 18176119.8 dated Jul. 30, 2018.

\* cited by examiner

SENSOR SYSTEM AND METHOD

FIELD

The subject matter described herein relates to sensor systems.

BACKGROUND

In traditional rotary machine applications, wireless monitoring systems are necessary in order to validate system level models, provide condition based monitoring and may be used for asset control. In order to increase the fidelity and/or reliability of the sensed data that is obtained by a sensor, multi-channel sensing systems are preferred. Surface acoustic wave (SAW) sensing systems are ideal for rotary applications as SAW systems among other things, SAW systems can be interrogated via wireless means, are inherently passive, and do not require the use of batteries or other energy harvesting techniques at the sensing point of the system. These attributes make them sensor candidates in areas where movement and/or hot environments preclude the use of wired and/or conventional electronics. A key attribute associated with passive sensing systems such as SAW sensing systems is that of efficient radio frequency (RF) coupling. Improved communication of sensed data between the sensor system and a reader disposed away from the sensor system can be achieved through an optimal RF coupler antenna design within the sensing system.

One issue with multi-channel sensing systems is cross-talk between two or more channels. Cross-talk between channels of the sensing system causes issues because each one channel can cause interference to an adjacent channel. This interference can reduce the measurement accuracy of the sensing parameter or if the interference is severe enough, may render the system unusable. Another issue with wireless multi-channel sensing systems is establishing and maintaining electrical coupling between a rotor antenna and a stator antenna, and between a rotor antenna and a reader that is disposed away from the sensing antenna. A rotor antenna that does not maintain signal connectivity with a reader through the stator antenna will provide inaccurate, sporadic, or not data whatsoever.

BRIEF DESCRIPTION

In one embodiment, a sensor system includes one or more rotor antennas on a shaft that moves within a stator bracket one or more of around an axis of the sensor system or along the axis of the sensor system, the one or more rotor antennas configured to communicate sensed data with one or more stator antennas on the stator bracket. Each rotor antenna has a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other. The one or more rotor antennas are configured to extend one or more of radially around an outer surface of the shaft of a sensor or along the outer surface of the shaft of the sensor.

In one embodiment, a method includes extending one or more rotor antennas on a shaft that moves within a stator bracket one or more of around an axis of a sensor system or along the axis of the sensor system. The one or more rotor antennas extending one or more of radially around an outer surface of the shaft of a sensor of along the outer surface of the shaft of the sensor. The method includes communicating sensed data of the one or more rotor antennas with one or more stator antennas on the stator bracket. Each rotor antenna having a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other.

In one embodiment, a sensor system includes one or more rotor antennas on a shaft that moves within a stator bracket one or more of around an axis of the sensor system or along the axis of the sensor system. The one or more rotor antennas are configured to communicate sensed data with one or more stator antennas on the stator bracket. Each rotor antenna has a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other. The one or more rotor antennas are configured to extend one or more of radially around an outer surface of the shaft of a sensor or along the outer surface of the shaft of the sensor. The stator bracket is configured to extend one or more of about the axis of the sensor or in a direction along the axis of the sensor. The stator bracket includes the one or more stator antennas. Each stator antenna has a stator signal trace disposed on a first side of a stator dielectric substrate and a stator return trace disposed on the first side of the stator dielectric substrate. The one or more stator antennas are configured to electrically couple with the one or more rotor antennas.

BRIEF DESCRIPTION OF THE DRAWINGS

The inventive subject matter will be better understood from reading the following description of non-limiting embodiments, with reference to the attached drawings, wherein below.

DETAILED DESCRIPTION

One or more embodiments of the inventive subject matter described herein provide for a sensor system and method having moving rotor antennas disposed on a moving shaft and stator antennas disposed on a fixed stator bracket configured to electrically couple with the rotor antennas. The rotor antennas can have signal traces and return traces disposed on a first side of a dielectric substrate of the rotor antennas, and the stator antennas can have signal traces and return traces disposed on a first side of the receiving dielectric substrate of the stator antennas. The first side of the dielectric substrate of the rotor antennas faces the first side of the receiving dielectric substrate of the stator antennas such that the signal traces and the return traces of the rotor antennas face the signal traces and return traces of the stator antennas. For example, the sensor system may be a differential line coupling rotor and stator antennas.

The system and methods described herein enable wireless electrical coupling between the rotor antennas and the stator antennas in order to communicate (e.g., radio frequency communication) sensed data from the sensors on the shaft to a reader disposed a distance away from the shaft. For example, the sensor system may be a multi-channel coupling system having one rotor antenna that communicates with (e.g., is electrically coupled with) one stator antenna using a first communication channel, and another rotor antenna that communicates with (e.g., is electrically coupled with) another stator antenna using a second communication channel. The multiple communication channels of the multi-channel coupling system may communicate data using the same and/or different frequencies and may operate at the same time and/or different moments in time. The differential line coupling rotor and stator antennas reduces cross talk between the different communication channels of the multi-channel coupling system while maintaining coupling performance requirements compared to sensor systems that do not include differential line coupling rotor and stator antennas.

Figure 1:
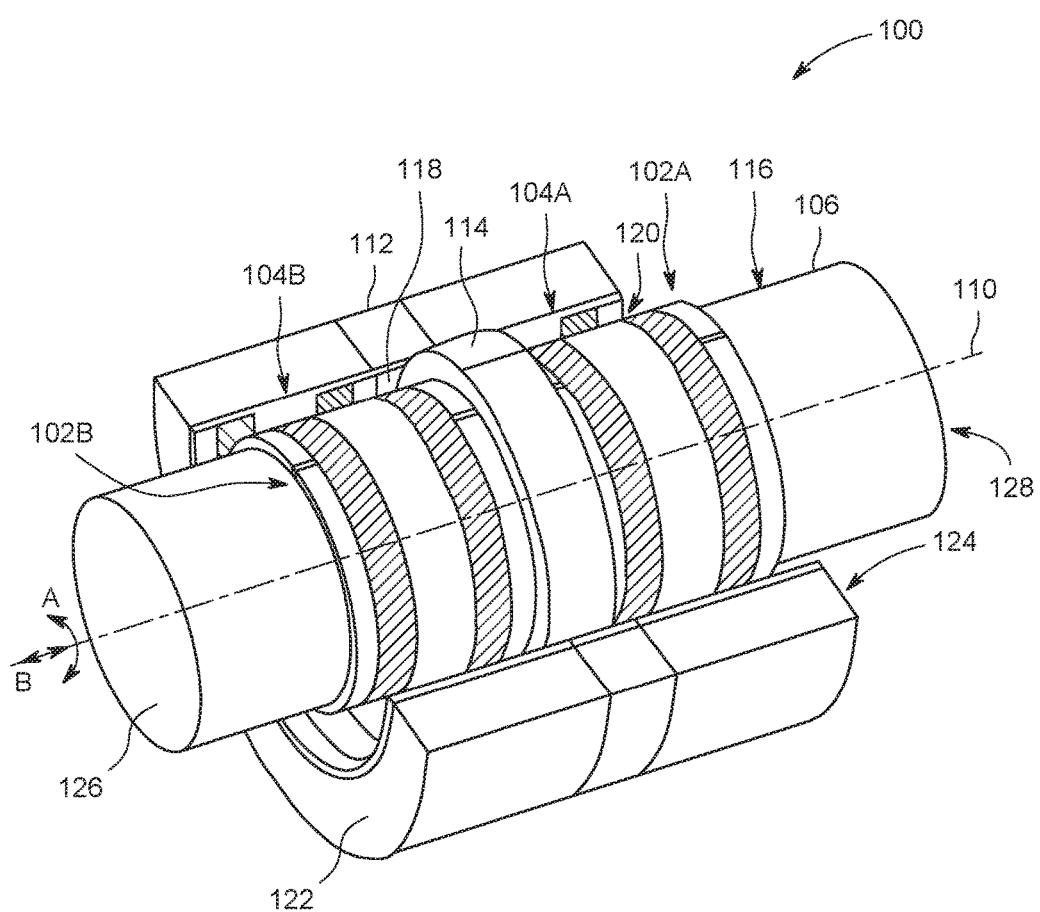
FIG. 1 illustrates a perspective view of a sensor system in accordance with one embodiment.

FIG. 1 illustrates a perspective view of a sensor system 100 in accordance with one embodiment. The sensor system 100 includes a shaft 106 that has a substantially circular cross-sectional shape. Alternatively, the shaft 106 may have any alternative cross-sectional shape and/or size. The shaft 106 is elongated along an axis 110 of a sensor of the sensor system 100 between a first surface 126 and a second surface 128. In the illustrated embodiment, the shaft 106 is a solid component. Optionally, the shaft 106 may be hollow between the first and second surface 126, 128. The shaft 106 is configured to rotate about the axis 110 in the direction A within the system 100. For example, the shaft 106 may rotate about the axis at speeds up to 5,000 revolutions per minute (rpm), 10,000 rpm, 20,000 rpm, 50,000 rpm, or the like. Optionally, the shaft 106 may rotate at speeds less than 5,000 rpm and/or greater than 50,000 rpm. The system 100 may be used in applications such as aviation, oil and gas, transportation, renewable energy extraction, or the like, in order to wirelessly communicate data obtained by a sensor of the rotating shaft 106.

The system 100 includes a stator bracket 112 that has a semi-circular cross-sectional shape that extends about the axis 110. For example, the stator bracket 112 is substantially C-shaped. Optionally, the stator bracket 112 may have any alternative shape and/or size. For example, the stator bracket 112 may be have a non-semi-circular cross-sectional shape, the stator bracket 112 may have a circular cross-sectional shape that extends fully around and/or partially around the shaft 106. In one or more embodiments, the stator bracket 112 may extend completely around the shaft 106 such that the stator bracket 112 electrically contains the moving shaft 106 and sensors of the sensing system 100 and thereby electrically containing the associated electromagnetic fields. For example, the stator bracket 112 may act as a faraday cage in order to improve the electromagnetic compatibility (EMC) compliance of the wireless sensing system 100.

The stator bracket 112 is elongated along the axis 110 between a first end 122 and a second end 124. The stator bracket 112 remains in a fixed and/or stationary position. For example, the stator bracket 112 remains stationary when the shaft 106 rotates about the axis 110. The stator bracket 112 has a gap 120 that extends about the axis 110 and extends between the first and second ends 122, 124 in a direction parallel to the axis 110. For example, the stator bracket 112 is separated a distance apart from the shaft 106 by the shape and size of the gap 120. The rotating shaft 106 rotates about the axis 110 within the gap 120 of the stator bracket 112. In the illustrated embodiment of FIG. 1, the stator bracket 112 is illustrated as a single component. Additionally or alternatively, the stator bracket 112 may have multiple components that have unique and/or common shapes and/or sizes that extend along the axis 110.

The system 100 includes one or more rotor antennas 102 that are disposed on an outer surface 116 of the shaft 106. In the illustrated embodiment of FIG. 1, the system 100 includes two rotor antennas 102A, 102B. Optionally, the system 100 may include more than two and/or less than two rotor antennas 102. The rotor antennas 102 have a curved shape that is curved in order to fit the curved outer surface 116 of the shaft 106. For example, the rotor antennas 102 are disposed on the outer surface 116 of the shaft 106 and extend radially around the outer surface 116 of the rotating shaft 106. The rotor antennas 102 may have substantially the same curved shape as the curved shape of the shaft 106. Optionally, the rotor antennas 102 may have a shape that extends radially about the axis 110 that is unique to the curvature of the shaft 106. The rotor antennas 102 will be described in more detail below.

The system 100 includes one or more stator antennas 104 that are disposed on an inner surface 118 of the stator bracket 112. The stator antennas 104 have a curved shape that is curved to fit the curved inner surface 118 of the stator bracket 112. For example, the stator antennas 104 are disposed on the inner surface 118 of the stator bracket 112 and extend radially around the inner surface 118 of the stator bracket 112 such that the stator antennas face the gap 120 and the shaft 106. The stator antennas 104 may have substantially the same curved shape of the gap 120 of the stator bracket 112. Optionally, the stator antennas 104 may have a shape about the axis 110 that is unique to the curvature of the gap 120 of the stator bracket 112.

The rotor antennas 102 communicate sensed data with the one or more stator antennas 104 as the shaft 106 rotates about the axis 110. For example, a first rotor antenna 102A is electrically coupled with a first stator antenna 104A to communicate sensed data from the first rotor antenna 102A to the first stator antenna 104A. Additionally, a second rotor antenna 102B is electrically coupled with a second stator antenna 104B in order to communicate sensed data from the second rotor antenna 102B to the second stator antenna 104B. For example, the first rotor antenna 102A is electrically coupled with the first stator antenna 104A via a first radio frequency (RF) signal, and the second rotor antenna 102B is electrically coupled with the second stator antenna 104B via a second RF signal.

The rotor antennas 102 wirelessly communicate the sensed data that is sensed (e.g., collected, measured, read, obtained, or the like) by one or more sensors (not shown) of the system 100. For example, the system 100 may include one or more sensors that are disposed around, inside of, at one end of, or the like, the shaft 106 in order to sense data such as temperature, pressure, orientation, strain, or the like. The sensors may be surface acoustic wave (SAW) sensors that are configured to measure temperature and/or strain of the shaft 106 when the shaft 106 is rotating and/or stationary. Optionally, the sensors may be any alternative sensor that senses information about the system 100 and/or about one or more components of the system 100.

The system 100 includes a rotor isolation ring 114 that extends around the shaft 106. The rotor isolation ring 114 separates the first rotor antenna 102A from the second rotor antenna 102B along the axis 110. The rotor isolation ring 114 is manufactured of a conductive and/or magnetic material. For example, the rotor isolation ring 114 may be manufactured out of a steel alloy, copper alloy, or the like. Optionally, the rotor isolation ring 114 may be manufactured out of a common and/or unique material as the shaft 106. The rotor isolation ring 114 electrically isolates the first rotor antenna 102A that is electrically coupled with the first stator antenna 104A from the second rotor antenna 102B that is electrically coupled with the second stator antenna 104B. For example, the rotor isolation ring 114 provides an electromagnetic barrier between the first and second rotor antennas 102A, 102B in order to reduce an amount of cross-talk between the first rotor antenna 102A communicating with the first stator antenna 104A using a first communication channel and the second rotor antenna 102B communicating with the second stator antenna 104B using a different, second communication channel relative to a system that is devoid of a rotor isolation ring 114 that separates the first and second rotor antennas 102A, 102B.

Figure 2:
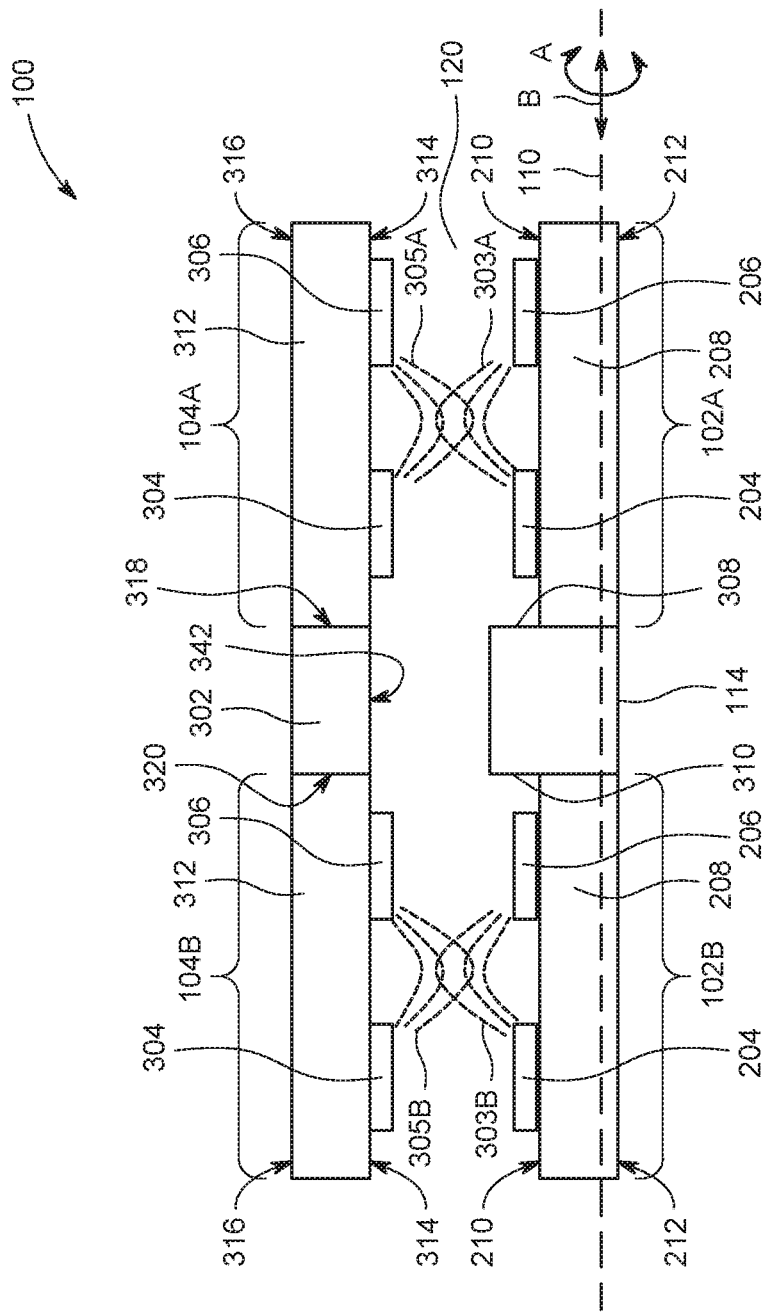
FIG. 2 illustrates a cross-sectional view of the sensor system of FIG. 1 in accordance with one embodiment.

FIG. 2 illustrates a cross-sectional view of the sensor system 100 in accordance with one embodiment. The first rotor antenna 102A is disposed on a first side 308 of the rotor isolation ring 114, and the second rotor antenna 102B is disposed on a second side 310 of the rotor isolation ring 114 along the axis 110 of the system 100. The first and second rotor antennas 102A, 102B include a dielectric substrate 208 that is disposed on the shaft 106 (of FIG. 1). The dielectric substrate may be manufactured of a dielectric material such as Styrofoam, silicone, fluorinated polymers, ceramics, or the like. In the illustrated embodiment, the dielectric substrate 208 is a single layer of dielectric material operably coupled to the outer surface 116 of the shaft 106. Optionally, the dielectric substrate 208 may be manufactured of multiple layers of dielectric and/or non-dielectric materials. The dielectric substrate 208 (e.g., the single layer and/or the multiple layers) may have a thickness between 1 mm and 8 mm (e.g., 0.04 in and 0.315 in), a thickness that is less than 1 mm, and/or a thickness that is greater than 8 mm. Optionally, the dielectric substrate 208 may have another thickness.

In the illustrated embodiment, the rotor isolation ring 114 separates the dielectric substrate of the first rotor antenna 102A from the dielectric substrate of the second rotor antenna 102B. Optionally, the first and second rotor antenna 102A, 102B may have a common dielectric substrate 208.

The rotor antennas 102 each include a rotor signal trace 204 and a rotor return trace 206 that are disposed on an outer rotor side 210 of the dielectric substrate 208 of the rotor antennas 102. For example, the rotor signal traces 204 and the rotor return traces 206 are disposed on the outer rotor side 210 of the dielectric substrate 208, and an opposite, inner rotor side 212 of the dielectric substrate 208 is disposed on the outer surface 116 of the shaft 106 (of FIG. 1). The dielectric substrate 208 is operably coupled to the shaft 106. For example, the inner rotor side 212 of the dielectric substrate 208 may be adhered to, bonded to, or the like, the outer surface 116 of the shaft 106. The rotor antennas 102 may be referred to as differential line coupling rotor antennas such that the rotor signal traces 204 and the rotor return trace 206 are disposed on the same outer rotor side 210 of the dielectric substrate 208. Alternatively, the rotor antennas 102 may be referred to as microstrip coupling rotor antennas such that the rotor signal traces 204 may be disposed on the outer rotor side 210 of the dielectric substrate 208, and the rotor return traces 206 may be disposed on the opposite, inner rotor side 212 of the dielectric substrate 208.

The rotor signal traces 204 and the rotor return traces 206 are not concentric with respect to each other. For example, concentric circles, arcs, or other shapes, same a common center axis, wherein the larger circle, arc, or shape surrounds the smaller circle, arc, or shape. Additionally, concentric circles, arcs, or shapes that share the common center axis extend radially away from the common center axis in the same plane. For example, two or more concentric circles share a common center axis, extend radially away from the common center axis within the same plane. Additionally, the two or more concentric circles extend varying distances away from the common center axis. For example, a first circle of the concentric circle may extend a first radius distance away from the common center axis with respect to a second circle of the concentric circles.

In contrast, the rotor signal traces 204 and the rotor return traces 206 are not concentric with respect to each other. The rotor signal traces 204 extend radially in a first plane of the shaft 106 and the rotor return traces 206 extend radially in a second, different plane of the shaft 106. The rotor signal traces 204 and the rotor return traces 206 are disposed in different radial planes along the axis 110 of the shaft 106. Additionally, the rotor signal traces 204 and the rotor return traces 206 do not share a common center axis. The rotor signal traces 204 and the rotor return traces 206 do not encircle a common point on the axis 110. Alternatively, the rotor signal traces 204 and the rotor return traces 206 encircle different points on the axis 110. For example, the rotor signal trace 204 of the first rotor antenna 104A is disposed at a location between the first surface 126 and the second surface 128 of the shaft along the axis 110, and the rotor return trace 206 of the first rotor antenna 104A is disposed at a different, second location between the first surface 126 and the second surface 128 of the shaft 106 along the axis 110. Additionally, the rotor signal traces 204 and rotor return traces extend radially a common distance away from the axis 110. For example, the rotor signal traces 204 and the rotor return traces 206 are at the same, common radius distance away from the axis 110.

The rotor signal traces 204 radiate sensor waves 303 away from the rotor signal traces 204 and the radiated rotor waves 303 are received by the rotor return traces 206 when an electric current is supplied to the rotor antennas 102. For example, the sensor waves 303A of the first rotor antenna 102A transmit from the rotor signal trace 204 to the rotor return trace 206 of the first rotor antenna 102A, and the sensor waves 303B of the second rotor antenna 102B transmit from the rotor signal trace 204 to the rotor return trace 206 of the second rotor antenna 102B.

The stator antennas 104A, 104B include a stator dielectric substrate 312 that is disposed on the stator bracket 112 (of FIG. 1). The stator dielectric substrate 312 may be manufactured of a dielectric material such as silicone, fluorinated polymers, ceramics, or the like. Optionally, the stator dielectric substrate 312 and the dielectric substrate 208 may be manufactured of the same or unique dielectric materials. In the illustrated embodiment, the stator dielectric substrate 312 is a single layer of dielectric material operably coupled to the inner surface 118 of the stator bracket 112. Optionally, the stator dielectric substrate 312 may be manufactured of multiple layers of dielectric and/or non-dielectric materials. The stator dielectric substrate 312 (e.g., a single layer and/or the multiple layers) may have a thickness between 1 mm and 8 mm (e.g., 0.04 in and 0.315 in), a thickness that is less than 1 mm, and/or a thickness that is greater than 8 mm. Optionally, the stator dielectric substrate 312 may have any alternative thickness.

In the illustrated embodiment, a stator isolation ring 302 separates the stator dielectric substrate 312 of the first stator antenna 104A from the stator dielectric substrate 312 of the second stator antenna 104B. Optionally, the first and second stator antennas 104A, 104B may have a common stator dielectric substrate 312.

The stator isolation ring 302 has an outer surface 342 that is generally planar with the first side 314 of the stator dielectric substrate 312 of the first and second stator antennas 104A, 104B. Optionally, the outer surface 342 may be non-planar with the first side 314. For example, the outer surface 342 may be disposed closer to the rotor isolation ring 114 than the first side 314 of the stator dielectric substrate 312 or may be disclosed further away from the rotor isolation ring 114 relative to the first side 314 of the stator dielectric substrate 312.

The stator antennas 104 each include a stator signal trace 304 and a stator return trace 306 that are disposed on the first side 314 of the stator dielectric substrate 312 of the stator antennas 104. For example, the stator signal traces 304 and the stator return traces 306 are disposed on the first side 314 of the stator dielectric substrate 312, and an opposite, second side 316 is operably coupled to the stator bracket 112. For example, the second side 316 of the stator dielectric substrate 312 may be adhered to, bonded to, or the like, the inner surface 118 of the stator bracket 112. The stator antennas 104 may be referred to as differential line coupling stator antennas such that the stator signal traces 304 and the stator return traces 306 are disposed on the same first side 314 of the stator dielectric substrate 312. Alternatively, the stator antennas 104 may be referred to as microstrip coupling stator antennas such that the stator signal traces 304 may be disposed on the first side 314 of the stator dielectric substrate 312, and the stator return traces 306 may be disposed on the opposite, second side 316 of the stator dielectric substrate 312.

The stator signal traces 304 radiate receiving waves 305 away from the stator signal traces 304 and the radiated stator waves 305 are received by the stator return traces 306 when an electric current is supplied to the stator antennas 104. For example, the receiving waves 305A of the first stator antenna 104A transmit from the stator signal trace 304 to the stator return trace 306 of the first stator antenna 104A, and the receiving waves 305B of the second stator antenna 104B transmit from the stator signal trace 304 to the stator return trace 306 of the second stator antenna 104B.

The first rotor antenna 102A is electrically coupled with the first stator antenna 104A such that the radiated rotor waves 303A of the first rotor antenna 102A are electrically coupled with the radiated stator waves 305A of the first stator antenna 104A in order to wirelessly communicate sensed data from the first rotor antenna 102A to the first stator antenna 104A. Additionally, the second rotor antenna 102B is electrically coupled with the second stator antenna 104B such that the radiated rotor waves 303B of the second rotor antenna 102B are electrically coupled with the radiated stator waves 305B of the second stator antenna 104B in order to wirelessly communicate sensed data from the second rotor antenna 102B to the second stator antenna 104B.

The first rotor and stator antennas 102A, 104A may communicate the sensed data using a first channel, and the second rotor and stator antennas 102B, 104B may communicate sensed data using a different, second channel. For example, the system 100 may be referred to as a multi-channel sensing system that communicates data using multiple channels, such that the first antennas 102A, 104A communicate wirelessly using a first channel of the multi-channel system, and the second antennas 102B, 104B communicate wirelessly using a second channel of the multi-channel system. In one or more embodiments, the first and second communication channels may use a common or unique frequency to communicate sensed data, may operate at the same or different moments in time, or the like. The configuration of the differential line first and second rotor antennas 102A, 102B electrically coupled with the differential line first and second stator antennas 104A, 104B reduces an amount of cross-talk between the first antennas 102A, 104A communicating sensed data using the first channel and the second antennas 102B, 104B communicating sensed data using the second channel relative to a multi-channel sensor system that does not have a differential line antenna configuration. For example, the differential line rotor antennas electrically coupled with the differential line stator antennas reduces an amount of cross-talk and/or interference between the differential line rotor and stator antennas relative to microstrip rotor antennas electrically coupled with microstrip stator antennas.

Additionally, the rotor isolation ring 114 may improve the electrical isolation between the first rotor and stator antennas 102A, 104A communicating using the first channel and the second rotor and stator antennas 102B, 104B communicating using the second channel relative to a system 100 that is without a rotor isolation ring 114. For example, the rotor isolation ring 114 reduce an amount of cross-talk between the adjacent communication channels of the multi-channel system, and may improve the accuracy of the sensed data that is communicated between the first antennas 102A, 104A and the second antennas 102B, 104B.

In one embodiment, the system 100 may include multiple rotor antennas electrically coupled with multiple stator antennas 104. For example, the system 100 may include more than two and/or less than two rotor antennas 102 configured to communicate sensed data with more than two and/or less than two stator antennas 104 using unique and/or common channels to communicate the sensed data. Additionally, the system 100 may include multiple rotor isolation rings 114 extending around the shaft 106 in order to electrically isolate the rotor and stator antennas 102, 104 from the additional rotor and stator antennas 102, 104. Optionally, the system 100 may include any number of rotor antennas 102, any number of stator antennas 104, or any number of rotor isolation rings 114.

The rotor and stator antennas 102, 104 are electrically coupled as the shaft 106 rotates about the axis 110 in the direction A. Additionally, the rotor and stator antennas 102, 104 are electrically coupled as the shaft 106 moves in an axial direction B along the axis 110. For example, the shaft 106 is configured to move in the axial direction B as the shaft 106 rotates.

Figure 3A:
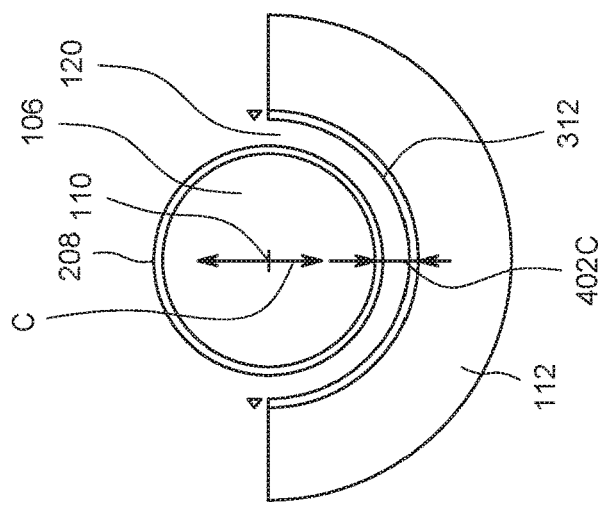
FIG. 3A illustrates a cross-sectional view of a sensor system in accordance with one embodiment.
Figure 3B:
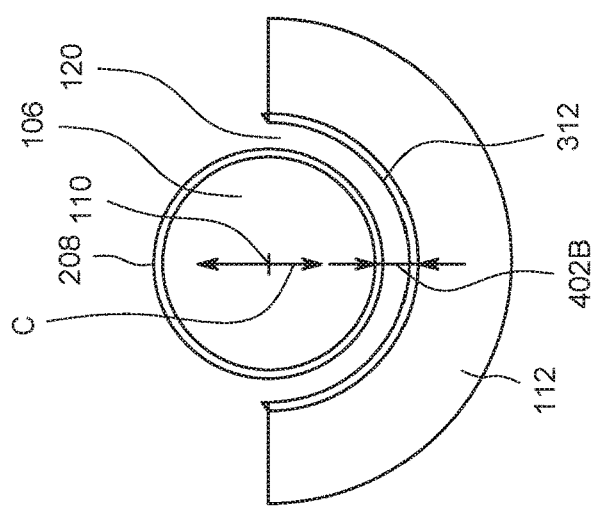
FIG. 3B illustrates a cross-sectional view of a sensor system in accordance with one embodiment.
Figure 3C:
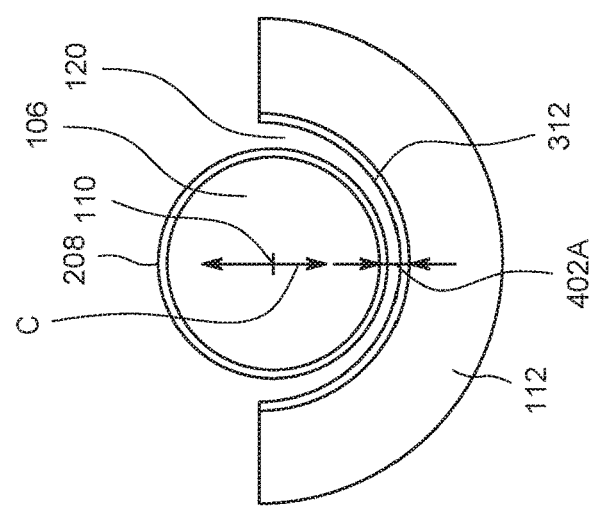
FIG. 3C illustrates a cross-sectional view of a sensor system in accordance with one embodiment.

FIGS. 3A, 3B, and 3C illustrate a cross-sectional view of the system 100 in accordance with one embodiment. The circular cross-section of the shaft 106 is substantially centered at the axis 110. The stator bracket 112 extends about the axis 110 such that the shaft 106 rotates within the gap 120 of the stator bracket 112. The shaft is configured to move in a radial direction C that is perpendicular to the axis 110 of the system 100. Additionally, the rotor and stator antennas 102, 104 are electrically coupled as the shaft 106 rotates in the direction A (in FIGS. 1 and 2), as the shaft 106 moves in the axial direction B (in FIGS. 1 and 2), and/or as the shaft 106 moves in the radial direction C. For example, as the shaft 106 moves in the radial direction C, a gap 402 extends between the rotor antennas 102 and the stator antennas 104. The gap 402 may vary for each revolution of the shaft 106 as the shaft 106 rotates within the gap 120, may vary at varying revolutions of the shaft 106, or the like. For example, the shaft 106 may not be centered at the axis 110, the shaft 106 may not have a circular cross-sectional shape, the gap 120 of the stator bracket 112 may not have a circular cross-sectional shape, or the like.

FIG. 3A illustrates one embodiment of the system 100 having a gap 402A that extends between the dielectric substrate 208 and the stator dielectric substrate 312 as the shaft 106 rotates about the axis 110 and moves in the radial direction C. The gap 402A may be a distance that is less than about 7 mm (e.g., less than about 0.3 inches) as the shaft 106 rotates.

FIG. 3B illustrates one embodiment of the system 100 having a gap 402B that extends between the dielectric substrate 208 and the stator dielectric substrate 312 as the shaft 106 rotates about the axis 110 and moves in the radial direction C. The gap 402B may be a distance that is between about 7 mm (e.g., about 0.3 inches) and about 17.8 mm (e.g., about 0.7 inches). For example, the gap 402B may be a distance about 12.7 mm (e.g., about 0.5 inches) as the shaft 106 rotates.

FIG. 3C illustrates one embodiment of the system 100 having a gap 402C that extends between the dielectric substrate 208 and the stator dielectric substrate 312 as the shaft 106 rotates about the axis 110 and moves in the radial direction C. The gap 402C may be a distance that is greater than about 17.8 mm (e.g., greater than about 0.7 inches) as the shaft 106 rotates.

Figure 4:
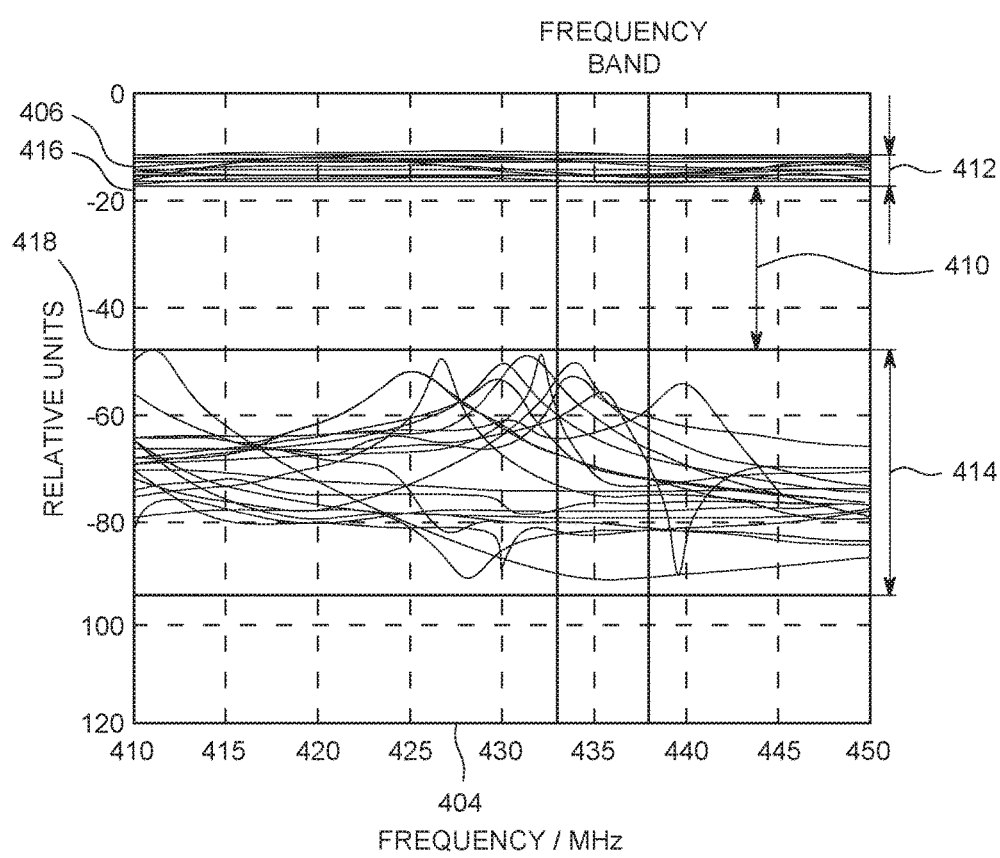
FIG. 4 illustrates a graph of the sensor system in accordance with one embodiment.

FIG. 4 illustrates a graph of the sensor system 100 operating over several frequencies in order to communicate sensed data from the rotor antennas 102 to the stator antennas 104 using multiple communication channels. A horizontal axis 404 is representative of a range of frequencies and a vertical axis 406 is representative of relative decibel (dB) units. A coupling variability band 412 illustrates a range of the measured channel-to-channel coupling of the differential line rotor and stator antennas 102, 104 of the sensor system 100. For example, the coupling variability band 412 illustrates that over a range of about 5 dB, the first rotor antenna 102A is electrically coupled with the first stator antenna 104A and the second rotor antenna 102B is electrically coupled with the second stator antenna 104B. Optionally, the coupling variability band 412 may be a range that is less than 5 dB and/or greater than 5 dB.

An isolation variability band 414 illustrates a range of the measured channel-to-channel isolation of the differential line rotor and stator antennas 102, 104 of the sensor system 100. For example, the isolation variability band 414 illustrates that over a range of about 55 dB, the first rotor and stator antennas 102A, 104A were electrically isolated from the second rotor and stator antennas 102B, 104B. Optionally, the isolation variability band 414 may be a range that is less than 55 dB and/or greater than 55 dB.

A signal to crosstalk range 410 from a highest coupling loss point 416, demonstrating the largest channel-to-channel coupling of the coupling variability band 412, to a lowest isolation point 418, demonstrating the smallest channel-to-channel isolation of the isolation variability band 414, illustrates the margin of isolation of the system 100 between the first antennas 102A, 104A, and the second antennas 102B, 104B. The signal to crosstalk range 410 demonstrates that the differential line coupling rotor and stator antennas 102, 104 may provide at least 30 dB of isolation (e.g., 15 dB coupling margin). For example, the arrangement of the rotor signal traces 204 and rotor return traces 206 of the rotor antennas 102 disposed on the outer rotor side 210 of the dielectric substrate 208, and the arrangement of the stator signal traces 304 and stator return traces 306 of the stator antennas 104 disposed on the first side 314 of the stator dielectric substrate 312 improves the channel-to-channel isolation of the multi-channel communication system 100 relative to a multi-channel communication system having microstrip rotor antennas communicating sensor data with microstrip stator antennas. Optionally, the signal to crosstalk range 410 may be larger and/or smaller than a 30 dB range of isolation.

Figure 5:
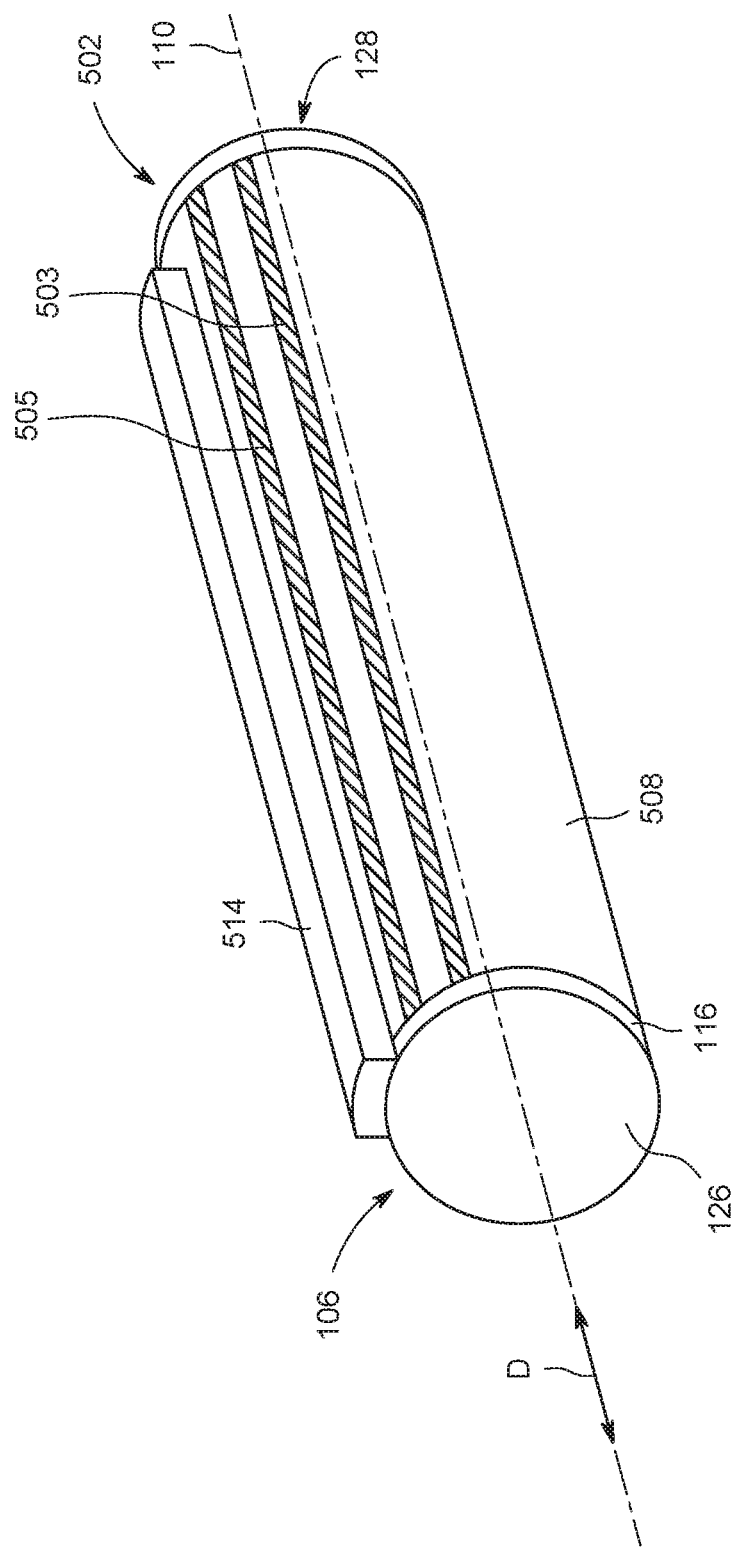
FIG. 5 illustrates a perspective view of a sensor system in accordance with one embodiment.
Figure 6:
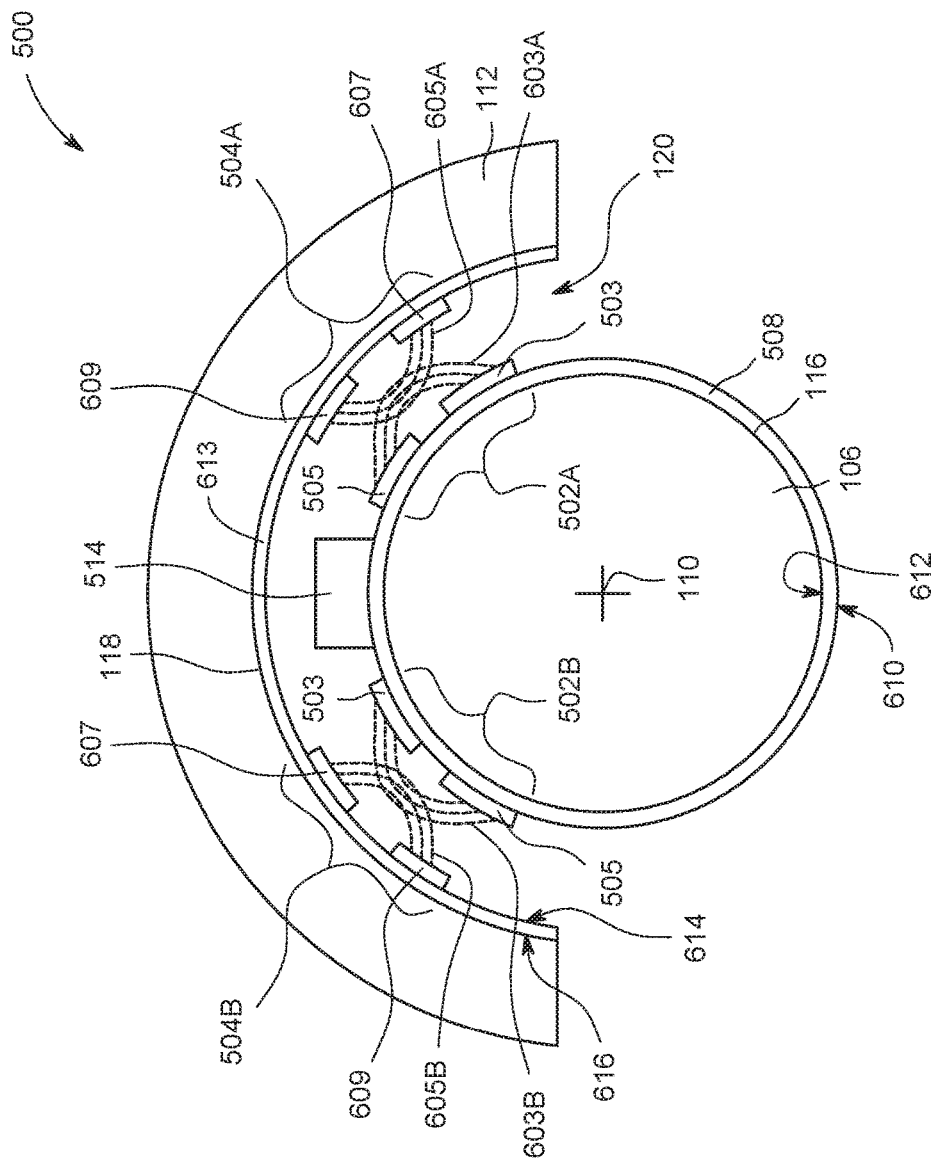
FIG. 6 illustrates a cross-sectional view of the sensor system of FIG. 5 in accordance with one embodiment.

FIG. 5 illustrates a perspective view of a sensor system 500 in accordance with one embodiment. FIG. 6 illustrates a cross-sectional view of the sensor system 500 of FIG. 5. FIGS. 5 and 6 will be discussed in detail together.

The sensor system 500 includes the shaft 106 that is elongated along the axis 110 of a sensor of the system 500 between the first surface 126 and the second surface 128. The shaft is configured to move in a back and forth direction B along the axis 110 within the system 500. For example, the shaft 106 may be a circular, or substantially circular, piston rod, pump jack rod, or the like. The system 500 may be used in applications such as aviation, oil and gas, transportation, renewable energy extraction, of the like, in order to wirelessly communicate data obtained by a sensor of the shaft 106.

The system 500 includes the stator bracket 112 (shown in FIG. 6) that extends about and is elongated along the axis 110. The stator bracket 112 remains in a fixed and/or stationary position. The shaft 106 moves in the direction B within the gap 120. In the illustrated embodiment of FIG. 6, the stator bracket 112 is illustrated as a single component. Additionally or alternatively, the stator bracket 112 may be made up of multiple components that have unique and/or common shapes and/or sizes that extend along the axis 110. The system 500 includes one or more rotor antennas 502 that are disposed on the outer surface 116 of the shaft 106. In the illustrated embodiment of FIG. 6, the system 500 includes first and second rotor antennas 502A, 502B. Optionally, the system 500 may include more than two and/or less than two rotor antennas 502. The rotor antennas 502 extend along the axis 110 between the first and second surfaces 126, 128 of the shaft 106 along the outer surface 116 of the shaft 106. In the illustrated embodiment, the rotor antennas 502 extend a length that is the same, or substantially the same, length as the shaft 106 between the first and second surfaces 126, 128. Additionally or alternatively, the rotor antennas 502 may extend a length that is less than the length of the shaft 106. For example, the rotor antennas 502 may extend more than half of the length of the shaft, less than half of the length of the shaft, a fraction of the length of the shaft, or the like.

The rotor antennas 502 include a dielectric substrate 508 that is disposed on the shaft 106. The dielectric substrate may be manufactured of a dielectric material such as Styrofoam, silicone, fluorinated polymers, ceramics, or the like. In the illustrated embodiment of FIGS. 5 and 6, the dielectric substrate 508 is a single layer of dielectric material operably coupled to the outer surface 116 of the shaft 106. Optionally, dielectric substrate 508 may be manufactured out of multiple layers of dielectric and/or non-dielectric materials. In the illustrated embodiment, the dielectric substrate 508 extends around the perimeter of the shaft 106. Optionally, the dielectric substrate 508 may extend around a part of the perimeter of the shaft 106.

The rotor antennas 502 each include a rotor signal trace 503 and a rotor return trace 505 that are disposed on an outer rotor side 610 of the dielectric substrate 508. For example, the rotor signal traces 503 and the rotor return traces 505 are disposed on the outer rotor side 610 of the dielectric substrate 508, and an opposite, inner rotor side 612 of the dielectric substrate 508 is disposed on the outer surface 116 of the shaft 106. For example, the inner rotor side 612 of the dielectric substrate 508 may be adhered to, bonded to, or the like, the outer surface 116 of the shaft 106. The rotor antennas 502 may be referred to as differential line coupling rotor antennas such that the rotor signal traces 503 and the rotor return traces 505 are disposed on the same outer rotor side 610 of the dielectric substrate 508. Alternatively, the rotor antennas 502 may be referred to as microstrip coupling antennas such that the rotor signal traces 503 may be disposed on the outer rotor side 610 of the dielectric substrate 508 and the rotor return traces 505 may be disposed on the opposite, inner rotor side 612 of the dielectric substrate 508.

The rotor signal traces 503 and the rotor return traces 505 are not concentric with respect to each other. For example, the rotor signal traces 503 and the rotor return traces 505 do not share a common center axis, and do not extend radially within a common radial plane about the axis 110. Additionally, the rotor signal traces 503 and the rotor return traces 505 do not encircle a common point on the axis 110. Alternatively, the rotor signal traces 503 and the rotor return traces 505 do not encircle the axis 110, but instead extend in a common direction as the axis 110.

The system includes one or more stator antennas 504 that are disposed on the inner surface 118 of the stator bracket 112 (shown in FIG. 6). The stator antennas 504 have a curved shape that is curved to fit the curved inner surface 118 of the stator bracket 112 about the axis 110. Optionally, the stator antennas 504 may have a shape about the axis 110 that is unique to the curvature of the gap 120 of the stator bracket 112.

In the illustrated embodiment of FIG. 6, the system 500 includes first and second stator antennas 504A, 504B corresponding to the first and second rotor antennas 502A, 502B. Optionally, the system 500 may include more than two and/or less than two stator antennas 504. The stator antennas 504 extend in a direction along the axis 110 between the first and second surfaces 126, 128 of the shaft 106 (not shown). For example, the stator antennas 504 extend a length that is the same length, or substantially the same length, as the rotor antennas 502. Additionally or alternatively, the stator antennas 504 may extend a length that is less than or greater than the length of the rotor antennas 502.

The stator antennas 504 include a stator dielectric substrate 613 that is disposed on the stator bracket 112. The stator antennas 504 each include a stator signal trace 607 and a stator return trace 609 that are disposed on a first side 614 of the stator dielectric substrate 613 of the stator antennas 504. For example, the stator signal traces 607 and the stator return traces 609 are disposed on the first side 614 of the stator dielectric substrate 613, and an opposite, second side 616 of the stator dielectric substrate 613 is operably coupled to the stator bracket 112.

The system 500 includes a rotor isolation ring 514 that extends in a direction along the axis 110 between the first and second surfaces 126, 128 of the shaft 106. The rotor isolation ring 514 separates the first rotor antenna 502A from the second rotor antenna 502B about the axis 110. The rotor isolation ring 514 electrically isolates the first rotor antenna 502A that is electrically coupled with the first stator antenna 504A from the second rotor antenna 502B that is electrically coupled with the second stator antenna 504B. For example, the rotor isolation ring 514 provides an electromagnetic barrier between the first antennas 502A, 504A and the second antennas 502B, 504B in order to reduce an amount of cross-talk between the first rotor antenna 502A communicating with the first stator antenna 504A and the second rotor antenna 502B communicating with the second stator antenna 504B relative to a system that is devoid of a rotor isolation ring 514 separating the first and second rotor antennas 502A, 502B.

The rotor signal traces 503 radiate rotor waves 603 away from the rotor signal traces 503 and the radiated rotor waves 603 are received by the rotor return traces 505 when an electric current is supplied to the rotor antennas 502. Additionally, the stator signal traces 607 radiate stator waves 605 away from the stator signal traces 607 and the radiated stator waves 605 are received by the stator return traces 609.

The first rotor antenna 502A is electrically coupled with the first stator antenna 504A such that the radiated rotor wavers 603A of the first rotor antenna 502A are electrically coupled with the radiated stator wavers 605A of the first stator antenna 504A in order to wirelessly communicate sensed data between the first rotor antenna 502A and the first stator antenna 504A. Additionally, the second rotor antenna 502B is electrically coupled with the second stator antenna 504B such that the radiated rotor wavers 603B of the second rotor antenna 502B are electrically coupled with the radiated stator wavers 605B of the second stator antenna 504B in order to wirelessly communicate sensed data between the second rotor antenna 502B and the second stator antenna 504B.

The first rotor and stator antennas 502A, 504A may communicate sensed data using a first channel, and the second rotor and stator antennas 502B, 504B may communicate sensed data using a different, second channel. For example, the system 500 may be referred to as a multi-channel sensing system that communicates data using multiple channels, such that the first antennas 502A, 504A communicate wirelessly using a first channel of the multi-channel system, and the second antennas 502B, 504B communicate wirelessly using a second channel of the multi-channel system. In one or more embodiments, the first and second communication channels may use a common or unique frequency to communicate sensed data, may operate at the same or different moments in time, or the like. The configuration of the differential line first and second rotor antennas 502A, 502B electrically coupled with the differential line first and second stator antennas 504A, 504B reduces an amount of cross-talk between the first antennas 502A, 504A communicating sensed data using the first channel and the second antennas 502B, 504B communicating sensed data using the second channel relative to a multi-channel sensor system that does not have a differential line antenna configuration. Additionally, the rotor isolation ring 514 may improve the electrical isolation of the first antennas 502A, 504A communication using the first channel from the second antennas 502B, 504B communicating using the second channel relative to a system that is without a rotor isolation ring 514. For example, the differential line rotor antennas 502 electrically coupled with the differential line stator antennas 504 reduces an amount of cross-talk and/or interference between the differential line rotor and stator antennas 502, 504 relative to microstrip rotor antennas electrically coupled with microstrip stator antennas.

Figure 7:
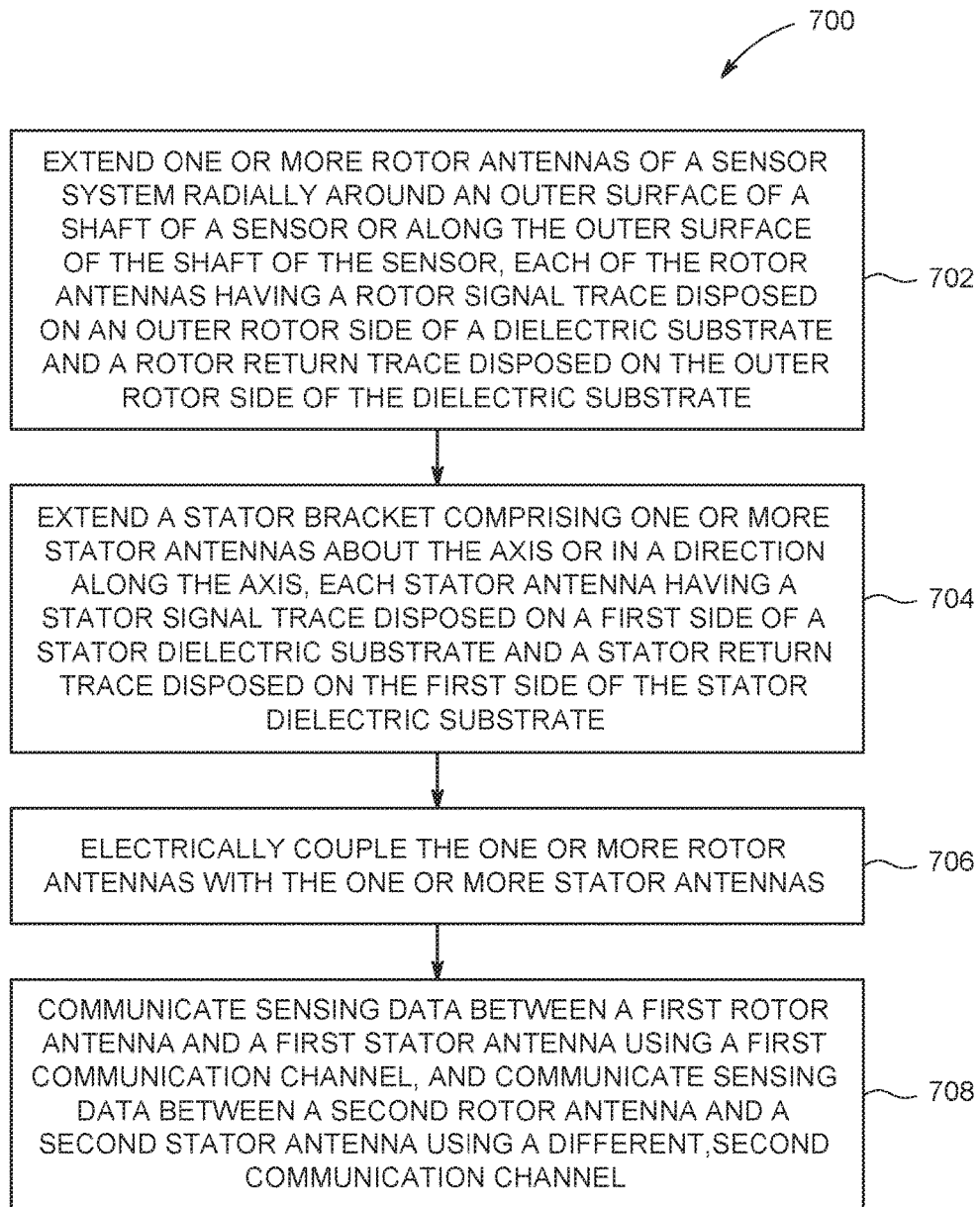
FIG. 7 illustrates a method flowchart in accordance with one embodiment.

FIG. 7 illustrates a method flowchart 700 of the sensor system 100 in accordance with one embodiment. At 702, one or more rotor antennas (e.g., rotor antennas 102, 502) of the sensor system are disposed on an outer surface 116 of a rotating shaft 106. The rotor antennas extend radially around the outer surface 116 of the shaft 106 and/or along the outer surface 116 of the shaft 106 that defines an axis 110 of the sensor system. Each rotor antenna has a rotor signal trace that is disposed on an outer rotor side of a dielectric substrate and a rotor return trace that is disposed on the outer rotor side of the dielectric substrate. The dielectric substrate has an opposite, inner rotor side that is disposed on the outer surface 116 of the shaft 106. For example, the rotor signal trace and the rotor return trace of each rotor antenna are disposed on the same side of the dielectric substrate that extends radially around and/or along the shaft 106.

At 704, a stator bracket 112 having one or more stator antennas (e.g., stator antennas 104, 504) extends about and/or in a direction along the axis 110. Each stator antenna has a stator signal trace that is disposed on a first side of a stator dielectric substrate and a stator return trace that is disposed on the first side of the stator dielectric substrate. For example, the stator signal trace and the stator return trace of each stator antenna are disposed on a same side of the stator dielectric substrate that is disposed on an inner surface 118 of the stator bracket 112 and faces the rotor antennas that extend radially around and/or along the outer surface 116 of the shaft 106.

At 706, the one or more rotor antennas are electrically coupled with the one or more stator antennas 104. For example, the radiated rotor waves and the radiated stator waves electrically couple the rotor and stator antennas when electric stimuli (e.g., electric current) is supplied to the rotor antennas and/or the stator antennas.

At 708, the rotor antennas, electrically coupled with the stator antennas, communicate sensed data with the stator antennas. For example, the first rotor and stator antennas (e.g., 102A, 502A, 104A, 504A) may communicate sensed data that is sensed (e.g., collected, measured, read, monitored, or the like) by a sensor of the sensor system using a first channel of the multi-channel sensor system; and the second rotor and stator antennas (e.g., 102B, 502B, 104B, 504) may communicate sensed data that is sensed by a sensor of the sensor system using a different, second channel of the multi-channel sensor system. The configuration of the differential line first and second rotor antennas electrically coupled with the differential line first and second stator antennas and communicating with different communication channels reduces an amount of cross-talk and/or interference relative to a multi-channel sensor system that does not have a differential line antenna configuration.

In one embodiment of the subject matter described herein, a sensor system includes one or more rotor antennas on a shaft that moves within a stator bracket one or more of around an axis of the sensor system or along the axis of the sensor system, the one or more rotor antennas configured to communicate sensed data with one or more stator antennas on the stator bracket. Each rotor antenna has a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other. The one or more rotor antennas are configured to extend one or more of radially around an outer surface of the shaft of a sensor or along the outer surface of the shaft of the sensor.

Optionally, the rotor signal trace and the rotor return trace do not encircle a common point on the axis.

Optionally, the stator bracket is configured to extend one or more of about the axis or in a direction along the axis. The stator bracket includes the one or more stator antennas. Each stator antenna has a stator signal trace disposed on a first side of a stator dielectric substrate and a stator return trace disposed on the first side of the stator dielectric substrate, wherein the one or more stator antennas are configured to electrically couple with the one or more rotor antennas.

Optionally, a first stator antenna of the one or more stator antennas is configured to electrically couple with a first rotor antenna of the one or more rotor antennas, and a second stator antenna of the one or more stator antennas is configured to electrically couple with a second rotor antenna of the one or more rotor antennas.

Optionally, a first stator antenna of the one or more stator antennas is configured to electrically couple with a first rotor antenna of the one or more rotor antennas, and a second stator antenna of the one or more stator antennas is configured to electrically couple with a second rotor antenna of the one or more rotor antennas. The first stator antenna and the first rotor antenna are configured to communicate the sensed data using a first channel and the second stator antenna and the second rotor antenna are configured to communicate the sensed data using a different, second channel.

Optionally, the one or more rotor antennas are one or more differential line rotor antennas and the one or more stator antennas are one or more differential line stator antennas, wherein the one or more differential line rotor antennas configured to communicate sensed data with the one or more differential line stator antennas reduces cross-talk relative to one or more microstrip rotor antennas configured to communicate sensed data with one or more microstrip stator antennas.

Optionally, the sensor system is a wireless surface acoustic wave (SAW) sensor system.

Optionally, the shaft is configured to rotate about the axis of the system.

Optionally, the shaft is configured to move in a direction perpendicular to the axis of the system.

Optionally, the shaft is configured to move in a direction parallel to the axis of the system.

Optionally, the system includes a rotor isolation ring configured to extend around the shaft. A first rotor antenna of the one or more rotor antennas is disposed on a first side of the rotor isolation ring and a second rotor antenna of the one or more rotor antennas is disposed on an opposite, second side of the rotor isolation ring.

Optionally, the sensor system is a multi-channel coupling system.

In one embodiment of the subject matter described herein, a method includes extending one or more rotor antennas on a shaft that moves within a stator bracket one or more of around an axis of a sensor system or along the axis of the sensor system. The one or more rotor antennas extending one or more of radially around an outer surface of the shaft of a sensor of along the outer surface of the shaft of the sensor. The method includes communicating sensed data of the one or more rotor antennas with one or more stator antennas on the stator bracket. Each rotor antenna having a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other.

Optionally, the rotor signal trace and the rotor return trace do not encircle a common point on the axis.

Optionally, the method includes extending the stator bracket one or more of about the axis of the sensor system or in a direction along the axis of the sensor system. The stator bracket includes the one or more stator antennas. Each stator antenna has a stator signal trace disposed on a first side of a stator dielectric substrate and a stator return trace disposed on the first side of the stator dielectric substrate, wherein the one or more stator antennas are configured to electrically couple with the one or more rotor antennas.

Optionally, the method includes electrically coupling a first stator antenna of the one or more stator antennas with a first rotor antenna of the one or more rotor antennas, and electrically coupling a second stator antenna of the one or more stator antennas with a second rotor antenna of the one or more rotor antennas.

Optionally, the method includes electrically coupling a first stator antenna of the one or more stator antennas with a first rotor antenna of the one or more rotor antennas, and electrically coupling a second stator antenna of the one or more stator antennas with a second rotor antenna of the one or more rotor antennas. The first stator antenna and the first rotor antenna are configured to communicate the sensed data using a first channel, and the second stator antenna and the second rotor antenna are configured to communicate the sensed data using a second channel.

Optionally, the one or more rotor antennas are one or more differential line rotor antennas and the one or more stator antennas are one or more differential line stator antennas, wherein the one or more differential line rotor antennas configured to communicate sensed data with the one or more differential line stator antennas reduces crosstalk relative to one or more microstrip rotor antennas configured to communicate sensed data with one or more microstrip stator antennas.

Optionally, the sensor system is a wireless surface acoustic wave (SAW) sensor system.

Optionally, the shaft is configured to rotate about the axis of the system.

Optionally, the shaft is configured to move in a direction perpendicular to the axis of the system.

Optionally, the shaft is configured to move in a direction parallel to the axis of the system.

Optionally, the method includes extending a rotor isolation ring around the shaft. A first rotor antenna of the one or more rotor antennas is disposed on a first side of the rotor isolation ring and a second rotor antenna of the one or more rotor antennas is disposed on an opposite, second side of the rotor isolation ring.

Optionally, the sensor system is a multi-channel coupling system.

In one embodiment, a sensor system includes one or more rotor antennas on a shaft that moves within a stator bracket one or more of around an axis of the sensor system or along the axis of the sensor system. The one or more rotor antennas are configured to communicate sensed data with one or more stator antennas on the stator bracket. Each rotor antenna has a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other. The one or more rotor antennas are configured to extend one or more of radially around an outer surface of the shaft of a sensor or along the outer surface of the shaft of the sensor. The stator bracket is configured to extend one or more of about the axis of the sensor or in a direction along the axis of the sensor. The stator bracket includes the one or more stator antennas. Each stator antenna has a stator signal trace disposed on a first side of a stator dielectric substrate and a stator return trace disposed on the first side of the stator dielectric substrate. The one or more stator antennas are configured to electrically couple with the one or more rotor antennas.

Optionally, a first stator antenna of the one or more stator antennas is configured to electrically couple with a first rotor antenna of the one or more rotor antennas, and a second stator antenna of the one or more stator antennas is configured to electrically couple with a second rotor antenna of the one or more rotor antennas. The first stator antenna and the first rotor antenna are configured to communicate the sensed data using a first channel and the second stator antenna and the second rotor antenna are configured to communicate the sensed data using a different, second channel.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor system comprising:
one or more rotor antennas on a shaft that moves within a stator bracket one or more of around an axis of the sensor system or along the axis of the sensor system, the one or more rotor antennas are configured to communicate sensed data with one or more stator antennas on the stator bracket, each rotor antenna having a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other,
wherein the one or more rotor antennas are configured to extend one or more of radially around an outer surface of the shaft of a sensor or along the outer surface of the shaft of the sensor; and
wherein the one or more rotor antennas are one or more differential line rotor antennas and the one or more stator antennas are one or more differential line stator antennas, wherein the one or more differential line rotor antennas configured to communicate sensed data with the one or more differential line stator antennas reduces cross-talk relative to one or more microstrip rotor antennas configured to communicate sensed data with one or more microstrip stator antennas.

2. The system of claim 1, wherein the rotor signal trace and the rotor return trace do not encircle a common point on the axis.

3. The system of claim 1, wherein the stator bracket is configured to extend one or more of about the axis or in a direction along the axis, the stator bracket comprising the one or more stator antennas, each stator antenna having a stator signal trace disposed on a first side of a stator dielectric substrate and a stator return trace disposed on the first side of the stator dielectric substrate, wherein the one or more stator antennas are configured to electrically couple with the one or more rotor antennas.

4. The system of claim 3, wherein a first stator antenna of the one or more stator antennas is configured to electrically couple with a first rotor antenna of the one or more rotor antennas, and a second stator antenna of the one or more stator antennas is configured to electrically couple with a second rotor antenna of the one or more rotor antennas.

5. The system of claim 3, wherein a first stator antenna of the one or more stator antennas is configured to electrically couple with a first rotor antenna of the one or more rotor antennas, and a second stator antenna of the one or more stator antennas is configured to electrically couple with a second rotor antenna of the one or more rotor antennas, wherein the first stator antenna and the first rotor antenna are configured to communicate the sensed data using a first channel, and the second stator antenna and the second rotor antenna are configured to communicate the sensed data using a different, second channel.

6. The system of claim 1, wherein the sensor system is a wireless surface acoustic wave (SAW) sensor system.

7. The system of claim 1, wherein the shaft is configured to rotate about the axis of the system.

8. The system of claim 1, wherein the shaft is configured to move in a direction perpendicular to the axis of the system.

9. The system of claim 1, wherein the shaft is configured to move in a direction parallel to the axis of the system.

10. The system of claim 1, further comprising a rotor isolation ring configured to extend around the shaft, wherein a first rotor antenna of the one or more rotor antennas is disposed on a first side of the rotor isolation ring and a second rotor antenna of the one or more rotor antennas is disposed on an opposite, second side of the rotor isolation ring.

11. The system of claim 1, wherein the sensor system is a multi-channel coupling system.

12. A method comprising:
extending one or more rotor antennas on a shaft that moves within a stator bracket one or more of around an axis of a sensor system or along the axis of the sensor system, the one or more rotor antennas extending one or more of radially around an outer surface of the shaft of a sensor or along the outer surface of the shaft of the sensor; and
communicating sensed data of the one or more rotor antennas with one or more stator antennas on the stator bracket, each rotor antenna having a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other;

wherein the one or more rotor antennas are one or more differential line rotor antennas and the one or more stator antennas are one or more differential line stator antennas, wherein the one or more differential line rotor antennas configured to communicate sensed data with the one or more differential line stator antennas reduces cross-talk relative to one or more microstrip rotor antennas configured to communicate sensed data with one or more microstrip stator antennas.

13. The method of claim 12, wherein the rotor signal trace and the rotor return trace do not encircle a common point on the axis.

14. The method of claim 12, further comprising extending the stator bracket one or more of about the axis of the sensor system or in a direction along the axis of the sensor system, the stator bracket comprising the one or more stator antennas, each stator antenna having a stator signal trace disposed on a first side of a stator dielectric substrate and a stator return trace disposed on the first side of the stator dielectric substrate, wherein the one or more stator antennas are configured to electrically couple with the one or more rotor antennas.

15. The method of claim 14, further comprising electrically coupling a first stator antenna of the one or more stator antennas with a first rotor antenna of the one or more rotor antennas, and electrically coupling a second stator antenna of the one or more stator antennas with a second rotor antenna of the one or more rotor antennas.

16. The method of claim 14, further comprising electrically coupling a first stator antenna of the one or more stator antennas with a first rotor antenna of the one or more rotor antennas, and electrically coupling a second stator antenna of the one or more stator antennas with a second rotor antenna of the one or more rotor antennas, wherein the first stator antenna and the first rotor antenna are configured to communicate the sensed data using a first channel, and the second stator antenna and the second rotor antenna are configured to communicate the sensed data using a different, second channel.

17. A sensor system comprising:
one or more rotor antennas on a shaft that moves within a stator bracket one or more of around an axis of the sensor system or along the axis of the sensor system, the one or more rotor antennas configured to communicate sensed data with one or more stator antennas on the stator bracket, each rotor antenna having a rotor signal trace disposed on an outer rotor side of a dielectric substrate of the rotor antenna and a rotor return trace disposed on the outer rotor side of the dielectric substrate, wherein the rotor signal trace and the rotor return trace are not concentric with respect to each other, wherein the one or more rotor antennas are configured to extend one or more of radially around an outer surface of the shaft of a sensor or along the outer surface of the shaft of the sensor, wherein the stator bracket is configured to extend one or more of about the axis of the sensor system or in a direction along the axis of the sensor system, the stator bracket comprising the one or more stator antennas, each stator antenna having a stator signal trace disposed on a first side of a stator dielectric substrate and a stator return trace disposed on the first side of the stator dielectric substrate, wherein one or more of the one or more stator antennas is configured to electrically couple with one or more of the one or more rotor antennas; and wherein a first stator antenna of the one or more stator antennas is configured to electrically couple with a first rotor antenna of the one or more rotor antennas, and a second stator antenna of the one or more stator antennas is configured to electrically couple with a second rotor antenna of the one or more rotor antennas, wherein the first stator antenna and the first rotor antenna are configured to communicate the sensed data using a first channel, and the second stator antenna and the second rotor antenna are configured to communicate the sensed data using a different, second channel.

* * * * *